United States Patent [19]

Kurjan et al.

[11] Patent Number: 5,540,657
[45] Date of Patent: Jul. 30, 1996

[54] DELIVERY DEVICE FOR INJECTABLE MATERIALS

[75] Inventors: Christine M. Kurjan, Palo Alto; Amy M. Droste, Fremont; James J. Feuhrer, San Carlos; Robert J. Fisher, Half Moon Bay; Dennis M. DeCamp, Covina, all of Calif.

[73] Assignee: Collagen Corporation, Palo Alto, Calif.

[21] Appl. No.: 360,512

[22] Filed: Dec. 21, 1994

Related U.S. Application Data

[63] Continuation of Ser. No. 275,899, Jul. 15, 1994, abandoned.
[51] Int. Cl.⁶ ................................................. A61M 5/178
[52] U.S. Cl. ..................... 604/70; 604/187; 604/117; 604/51; 137/614.11
[58] Field of Search ............................ 604/70, 187, 131, 604/140.1, 150–155, 236, 30, 51–53, 117, 118; 137/614.11

[56] References Cited

U.S. PATENT DOCUMENTS 5,024,656  6/1991  Gasaway et al. .
5,127,436  7/1992  Campion et al. .
5,141,496  8/1992  Dalto et al. .
5,305,788  4/1994  Mayeux .
5,383,851  1/1995  Mackinnon, Jr. et al. .

Primary Examiner—C. Fred Rosenbaum
Assistant Examiner—Perry E. Van Over
Attorney, Agent, or Firm—Shirley L. Church; Donald J. Verplancken; Kathi Rafayko

[57] ABSTRACT

The invention pertains to a delivery device for controlling the injection of discrete quantities of fluid injectable materials through a conduit such as a hypodermic needle or a catheter. The delivery device is coupled to a pressurized driving fluid source, and the control means provides controlled passage of pressurized driving fluid into a syringe body to act against a piston which forces the fluid injectable material out the needle or catheter.

In addition to the delivery device, the invention includes a needle depth guide which is preferably used in combination with the delivery device for cosmetic applications when a hypodermic needle is used to deliver a fluid injectable material to the dermis.

18 Claims, 6 Drawing Sheets

DELIVERY DEVICE FOR INJECTABLE MATERIALS

This application is a Continuation of prior U.S. application Ser. No. 08/275,899, filed Jul. 15, 1994, which is now abandoned.

BACKGROUND OF THE INVENTION

1. Field of the Invention

The present invention relates to the field of injection wherein a quantity of an injectable material may be delivered into human or other mammals. More particularly, the invention relates to delivery devices, and the injection of materials therewith, where the quantity of the material delivered by the device must be closely monitored and/or the exact position at which the material enters the body must be closely controlled.

2. Background Art

Injectable materials for human and other mammalian uses are typically injected into the body through a delivery vehicle such as a hypodermic needle. This type of needle is generally a hollow tube terminating at one end in a sharp tip. The needle is typically coupled to one of several known delivery devices which feed to the needle, such as a syringe body (to form a hypodermic syringe), or tubing leading to a bag or other container, in the case of the larger volumes of injectable material.

The hypodermic syringe body provides a stable, sterile environment in which a volume of the injectable material may be held for direct injection through the needle. It also provides a physical platform that an operator, such as a physician or nurse, may grip to control the depth and orientation of the needle during the injection of the injectable material into the human, or other mammalian body. In order to pass the injectable material from the syringe body through the needle, a plunger, having a piston formed on the forward end thereof, is reciprocally received within the syringe body. By pushing the plunger inwardly of the syringe body, the piston is forced inwardly of the syringe body to displace the injectable material in the syringe body through the needle.

One prior art use of hypodermic syringes is as a delivery system for collagen, sold under the trade names Zyplast® and Zyderm® by Collagen Corporation, Palo Alto Calif., which may be used for cosmetic or other purposes. In this application, the syringe is used to deliver a quantity of collagen interdermally to eliminate an undesirable cosmetic appearance of the skin at that location. For example, where, as a result of an unrelated surgery, body tissue does not fully support the overlying skin (epidermis), collagen may be injected under the epidermis, deep into the dermis, to provide a supporting mass. Likewise, where an individual has undesired wrinkles which are superficial, collagen may be injected just under the epidermis, to increase the volume of tissue under the epidermis surface to minimize or eliminate the wrinkles.

Using a hypodermic syringe to inject the required amount of collagen at a particular location within the dermis requires a substantial degree of skill. In particular, the practitioner injecting collagen must simultaneously control the depth, orientation and position of the needle at a particular injection site, while providing an inward force on the plunger that is sufficient to force a controlled volumetric flow rate of high viscosity collagen out of the needle and into the exact location in the dermis that will provide the desired cosmetic effect. Each of the individual parameters of plunger force, needle depth, needle orientation and needle position independently contribute to the ultimate cosmetic effect of the injection. However, the structure of a typical hypodermic syringe can make simultaneous control of these different parameters difficult for even skilled practitioners. In particular, to force the collagen through the needle, the practitioner must articulate the thumb of the hand holding the syringe to the back if the rearwardly extending plunger while simultaneously wrapping two or more fingers about the syringe body or over the flange at the back of the syringe body. Then, the practitioner must press the plunger inwardly of the syringe body to physically displace the collagen in the syringe body, and thus, force the collagen out of the needle. As a result, during the period in which the practitioner must exercise precise control over the location of the needle tip, the needle tip is positioned several inches from the nearest portion of the practitioner's hand. Additionally, the syringe effectively pivots about the practitioner's fingers. Therefore, any movement of the practitioner's thumb on the plunger that is not collinear with the plunger will result in an equal and opposite movement of the needle tip. Such movement, when the needle is already positioned at a precise location in the dermis, will move the tip out of position and the collagen will be mis-delivered.

The locating of the needle tip at the proper depth within the dermis is also difficult for the practitioner. To engage the tip of the needle at the proper injection depth, the practitioner may move the needle inwardly and outwardly with respect to the surface of the skin (epidermis). However, there is no visual reference point, other than the end of the syringe body, from which the practitioner can easily determine the extent that the needle extends into the dermis. Thus, the needle tip may be placed too deep, or too shallow, for the intended application. Additionally, as the practitioner depresses the plunger to displace collagen from the needle, the entire syringe may rock back and forth and thus vary the depth of the needle tip at the injection site.

To further complicate the collagen injection regimen, a practitioner typically does not inject a preselected quantity of collagen to create a desired cosmetic effect, but instead typically determines the total injection quantity by monitoring the effect of the injected collagen on the injection site during the injection. As the injection site begins to take on the desired appearance, the practitioner must closely control the quantity of collagen leaving the needle to ensure that the overall quantity of collagen ultimately entering the injection site does not exceed the quantity necessary to provide the desired cosmetic effect. It should be appreciated that the person (practitioner) injecting the collagen must have good, steady control of the fingers, hand and arm and also have excellent eye-hand coordination to be an effective provider of cosmetic collagen injections. These qualities are not always present in individuals, and this has limited the availability of collagen therapy to patients.

In addition to the cosmetic applications for injectable collagen described above, there are newly developed applications for treatment of urinary incontinence and rectal incontinence. These latter applications require delivery of larger quantities of injectable collagen to a precise location within the body. And, although a catheter rather than a needle may be used at the point of injection in some instances (treatment of urinary incontinence for example), accurate delivery of quantity of injectable material is very important.

Therefore, there exists a need in the art to provide a delivery device for materials, including collagen and other injectable materials which provides at least one of the following: (i) improved control over the delivery of the material by the device, including the rate of delivery and the overall quantity of the material delivered; (ii) improved operability, to reduce the effect of the operator's actuation of the syringe plunger on the position of the needle in the dermis for cosmetic applications; and (iii) an easily usable means of determining the depth of penetration of the needle into the dermis for cosmetic applications, to ensure proper delivery of collagen, or other materials, to a desired injection site.

SUMMARY OF THE INVENTION

The present invention provides a delivery device for injecting discrete quantities of a material, such as collagen, in dermal, sub-dermal or other locations in humans and other mammals. The invention includes a syringe holding member, within which a syringe may be removably mounted, and a metered source of power, such as a pressurized pneumatic source, to selectively power the syringe piston forward in the syringe to displace selectable quantities of injectable material from the syringe.

In the preferred embodiment, the delivery device includes a conformable syringe-receiving housing which may be held in the hand, a trigger member which is selectively positionable to communicate fluid under pressure, including a liquid or a gas, to the syringe piston, and a pneumatic control system coupled to the trigger member to control the flow of pressurized fluid to the syringe plunger. The trigger member is actuable between an "on" position to provide a flow of pressurized fluid to the syringe body, and an "off" position to prevent the passage of fluid into the syringe body and to vent the gas volume between the piston and the control system.

In a more preferred embodiment of the invention, for cosmetic applications, the delivery device includes an adjustable needle depth gauge to provide a visual and/or physical indication of the extent of needle penetration into the dermis to allow the practitioner of the delivery device to ensure delivery of the injectable material to the proper location within the dermis at the injection site. Preferably, the depth gauge is mounted about the syringe needle, and is adjustable on threads provided on the distal end of the syringe body.

The extension of the needle past the end of the depth gauge is calibrated to equate with the preferred depth below the surface of the skin at which the product in the syringe is to be delivered. The practitioner of the delivery device can thus precisely deliver the injectable material into a specific location under the epidermis. Although the depth guide is of particular utility when coupled with the preferred delivery device configuration, the depth guide may also be used in conjunction with any needle or tube type delivery device where the portion of the needle or tube extending from a baseline position is critical to the delivery of the material to a desired location.

These and other features of the invention will be apparent from the following description of the embodiments, when read in conjunction with the following drawings, wherein:

DESCRIPTION OF THE PREFERRED EMBODIMENTS

The present invention provides a delivery device for delivering a fluid or other injectable material into desired locations in humans and other mammals. Although the invention is primarily directed to the injection of collagen, the invention is equally well suited to the injection of other viscous fluids or injectable materials through a needle or other delivery vehicle/conduit, such as a catheter, into humans and other mammals. The invention is also particularly well suited to the injection of such materials where different portions of the volume of the material in a delivery device such as a syringe are injected into one or more injection sites in a single patient during multiple insertions of the needle or catheter into that single patient. In addition, the invention is equally well suited to situations where the quantity of material introduced during each injection is critical or is determined by monitoring the effect of the material on the patient as it is injected.

Figure 1:
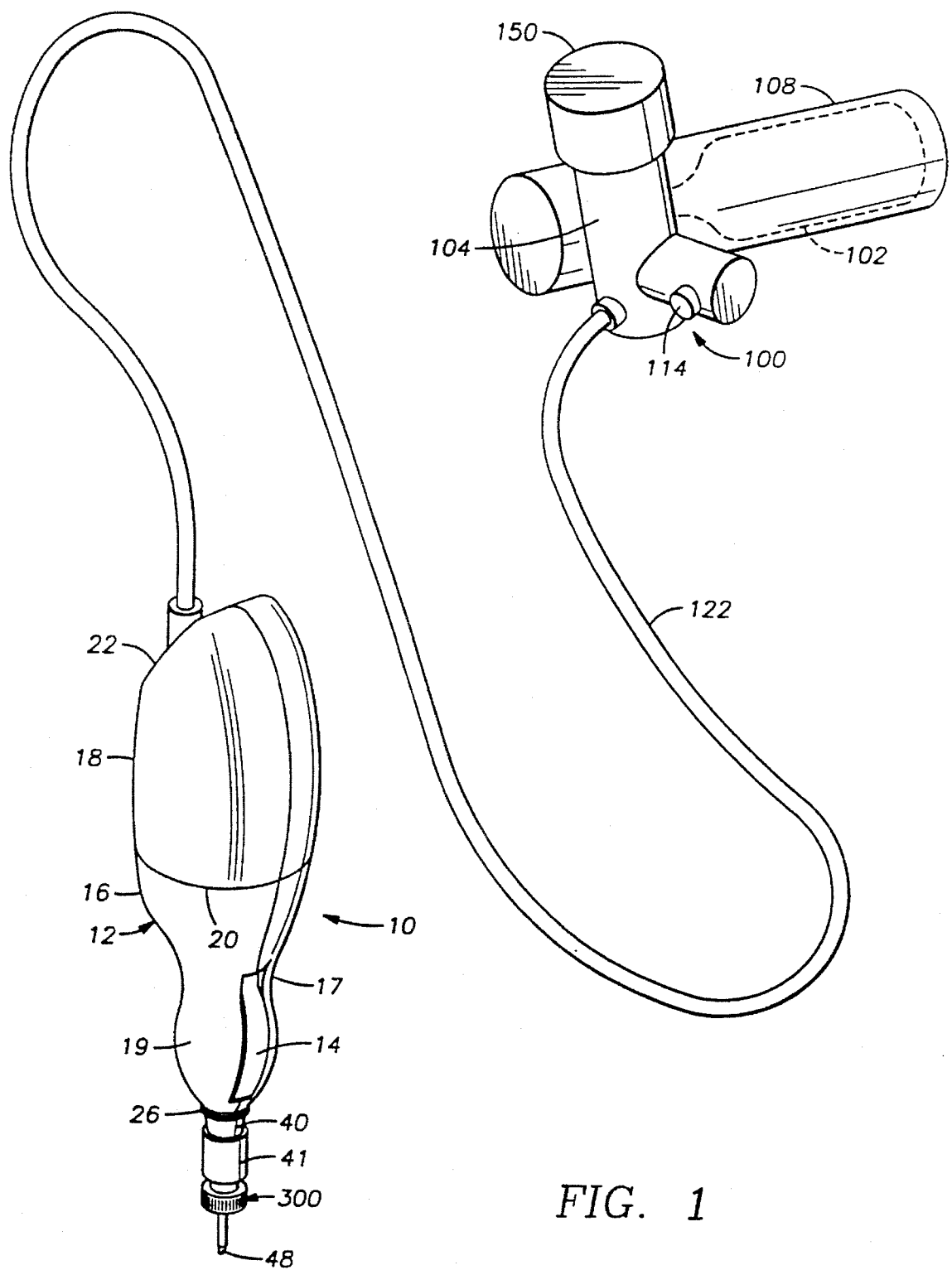
FIG. 1 is a perspective view of the preferred configuration of the delivery device of the present invention.

Referring now to FIG. 1, a perspective view of the most preferred embodiment of the invention, including delivery device 10 and pneumatic supply 100 is shown. The delivery device 10 generally includes a conformable body 12 having a syringe 40 with injectable material such as collagen selectively receivable therein. (Best shown in FIG. 2). The body 12 is configured to fit easily in a practitioner's hand, such that a trigger 14 thereon may be easily actuated between an "off", preferably extended, position and an "on", preferably depressed, position. The body 12 of the delivery device 10 preferably includes a separable syringe housing 16 and a valve housing 18 connected at a fitting 20, such as a bayonet or j-lock fitting, which permits easy separation and re-connection of the syringe housing 16 and the valve housing 18. (Best shown in FIG. 2).

The syringe housing 16 includes a front opening 26 through which the distal end portion 41 of a syringe 40 projects, and the valve housing 18 includes a rear fitting portion 22, preferably configured as a quick disconnect luer fitting, to allow quick connection, and disconnection, of a pneumatic supply 100 to the body 12. The trigger 14 is connected to the syringe housing 16 about a pivot point within the syringe housing 16 (shown in FIG. 2), and may be moved about the pivot point between an extended, or no flow, condition and a depressed, or flow condition. The trigger 14 may also be positioned between the extended and retracted positions to vary the flow rate of the collagen delivered to an injection site as will be further described herein.

The body 12, in conjunction with the positioning of the trigger 14 thereon, provides a delivery device which may be firmly gripped in an operator's hand and easily maneuvered to provide control of the position of a needle 48 positioned on the distal end portion 41 of the syringe body 40 which extends from the front of the syringe housing 16. In the preferred embodiment, the valve housing 18 is configured as a generally cylindrical member, and the syringe housing 16 includes a reduced diameter portion 17 which terminates in a semi-spherical portion 19 forming the forward end of the syringe housing 16. Thus, when a practitioner holds the delivery device 10 in his or her hand, the practitioner's thumb and index finger will engage the interface of the semi-spherical portion 19 and reduced diameter portion 17, while the remaining fingers of the hand can extend around, and thus grip, the cylindrical valve housing 18 portion of the body 12. Alternatively, the practitioner may wrap his or her fingers about the body 12, with the thumb extending forwardly such that the last digit of the thumb is positioned over the trigger 14. Thus, a single hand operable device for delivering a collagen dispersion into an injection site is provided. Further, as the fingers of the practitioner's hand are located adjacent the front, or needle (in the case of FIGS. 1 and 2) end of the delivery device 10, and the practitioner's thumb is not extending rearwardly to press the projecting end of a plunger, the likelihood that the needle 48 will move into an undesired location as the collagen is injected is significantly decreased. The trigger 14 may also be located even nearer the front of the body 12, and actuatable about a pivot at that position.

Figure 2:
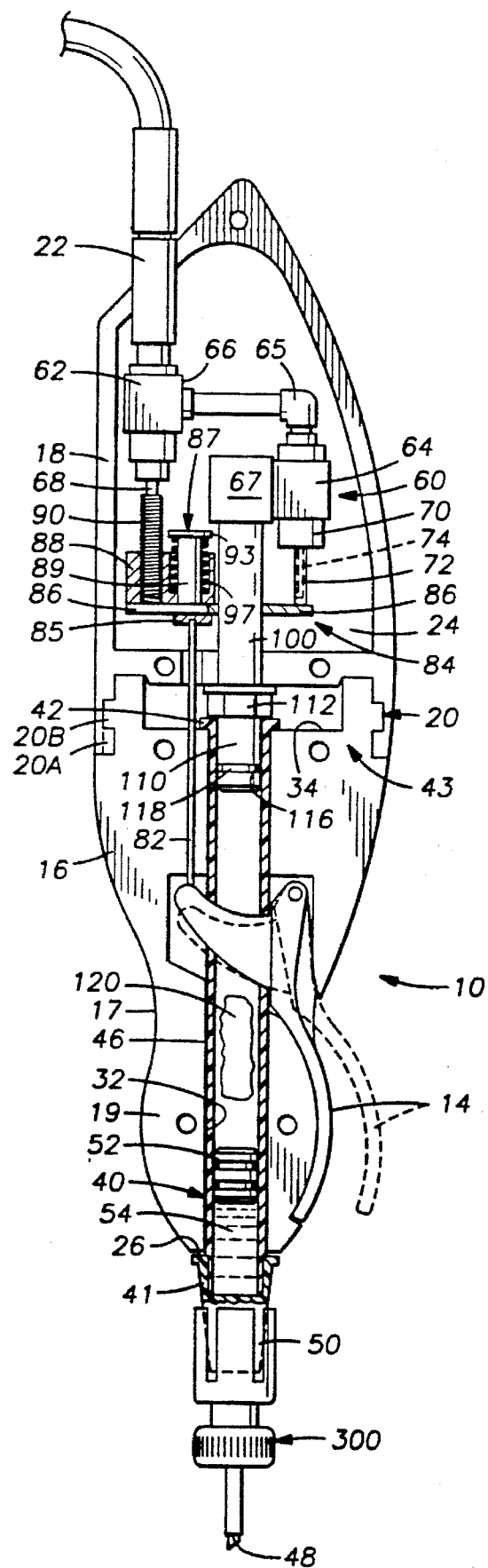
FIG. 2 is a sectional view of the delivery device of FIG. 1 at 2—2.

Referring now to FIG. 2, the preferred construction and interconnection of the valve housing 18 and syringe housing 16 for supporting the syringe 40 and a control valve system 60 is shown. The syringe housing 16 is preferably a one piece molded member having a cylindrical outer portion of varying diameter to form the semi-spherical portion 19 and the reduced diameter portion 17, which outer portion terminates in a front opening 26 and a rear mating portion 43. A bore 32 extends longitudinally through the syringe housing 16 from the front opening 26 to the mating portion 43 and is sized to receive a syringe 40 therein as will be further described herein. Mating portion 43 includes a bearing face 34 extending around the periphery of the bore 32 and a fitting portion 20a extending around the periphery of the mating portion 43.

The valve housing 18 is also a generally cylindrical member with a variable outer diameter terminating in a rear fitting portion 22 into which the pneumatic fitting is received, a front fitting portion 20a, and a control system cavity 24 within which the delivery device control valve system 60 is received. The rear fitting portion 22 is preferably configured at a lockable luer fitting. The valve housing 18 is preferably a two-piece member, which may be disassembled to service the control system 60 if necessary. To connect the valve housing 18 and syringe housing 16 to form the delivery device body 12, the fitting portions 20a, 20b are aligned to match the bayonet or j-lock portions thereof, and the housings 16, 18 are twisted relative to each other to connect the housings 16, 18 about the fitting 20.

Referring still to FIG. 2, the syringe 40 is preferably a standard injection syringe, 3 wherein the plunger has been removed. Syringe 40 includes an outer body portion 46 with an outwardly extending flange 42 on the rear end thereof and a luer fitting 50, with a needle 48 extending therefrom, located on the distal end portion 41 thereof. A piston 52 is received within the body portion 46 such that a defined volume 54 of collagen dispersion or solution is provided within the body portion 46 between the piston 52 and the distal end portion 41 of the body portion 46. The piston 52 is preferably a free floating piston that does not include a plunger bar attached directly thereto. The bore 32 of the syringe body 16 is sized to receive the outer body portion 46 of the syringe 40 therein, such that the syringe flange 42 is engaged against the bearing face 34 of the mating portion 43 of the syringe housing 16 adjacent to the inward terminus of the bore 32 in the syringe housing 16. Thus, as pressurized fluid is applied into the syringe 40, the syringe 40 is restrained against forward movement in the bore 32 by the interference of the flange 42 with the bearing face 34, and the piston 52 may move inwardly of the syringe body 36 to displace the material volume 54 outwardly through the syringe 40.

The control valve system 60 for the delivery device 10 is received in the control system cavity 24 of the valve housing 18. The control valve system 60 is configured to provide a selectively variable quantity of pressurized fluid, preferably a gas such as $CO_2$, through a transfer tube 110 extending from the control valve system 60 and into the rear, open end of the syringe 40, and thus to the piston 52. The control valve system 60 is actuable between an "open" position to allow fluid to flow therethrough to move the piston 52 to displace the material volume 54 of collagen in the syringe 40 out of the needle 48 and into the injection site, and a "closed" position to prevent the passage of fluid through the control valve system 60 and to vent the pressurized gas volume behind the piston 52 after a desired quantity of collagen has been displaced out of the needle 48 by the forward movement of the piston 52. This configuration and operation allows the practitioner using the delivery device to direct a discrete, controllable quantity of collagen into the desired injection site and then immediately terminate collagen delivery when the desired quantity of collagen has been delivered. The control of the quantity of collagen delivered may be provided by visually monitoring the effect of the collagen delivery on the skin surface at the delivery site.

One skilled in the art can also envision the use of measured quantities of material from within the syringe for other end use applications such as urinary incontinence. In such instance, the proper amount of material can be placed in the syringe initially, or housing 16 can be shaped in a manner which exposes the surface of syringe 40, permitting determination of the amount of material which remains therein.

The control system 60 enables the practitioner to stop the flow of collagen dispersion or solution immediately upon reaching a specific desired effect on the body or a particular quantity of collagen dispersion or solution dispensed. Referring still to FIG. 2, the details of the construction of the control system 60 are shown. The control system 60 includes a flow control valve 62 and a three way valve 64 configured in series, which are operated by the trigger 14. The flow control valve 62 is preferably a needle valve having a body 66 and a rotatable stem 68. By rotating the stem 68 of the flow control valve 62, a passage (not shown) extending through the needle valve body 66 may be selectively opened and closed to permit the pressurized gas or other fluid to pass through the valve. Further, the passage through the flow control valve 62 may be throttled, i.e., the rate of fluid flow through the passage may be varied by varying the arcuate position of the valve stem 68. The three-way valve 64 is preferably configured to allow passage of fluid therethrough when the three-way value 64 is open, and to vent fluid pressure from the downstream side of the three way valve 64 when the three way valve 64 is closed. To provide this operation, the three way valve includes a valve body 70, and a plunger 72 extending outwardly from the valve body 70.

The plunger 72 includes a relief passage 74 therein (shown in phantom), which may be selectively used to connect the downstream, or syringe piston, side of the three way valve 64 to atmosphere. The three-way valve 64 is spring biased to maintain the stem 72 in an extended position from the valve body 70, which maintains the relief passage 74 in the plunger 72 in communication with the downstream side of the valve 64 when the valve 64 is closed.

The flow control valve 62 and the three way valve 64 are coupled in series to selectively pass pressurized fluid from the pneumatic supply 100 (shown in FIG. 1) to the transfer tube 110 extending between the control system and the syringe piston 52 in the syringe body 42. Preferably, an elbow 65 is provided to communicate fluid from the flow control valve 62 to the three-way valve 64, and an elbow 67 is provided to communicate fluid from the three-way valve 64 to the transfer tube 110. The preferred sequence of operation of the valves 62 and 64, to supply pressurized gas to the piston 52 is to first close the relief passage 74 by partially depressing the plunger 72 of the three way valve 64, and then simultaneously further depressing the plunger 72 to open the passage through the three way valve 64 while turning the valve stem 68 to open the passage through the needle valve 62.

Referring now to FIGS. 2 to 5, the control system 60 is operated by the movement of a transfer rod 82 contactable at one end to the trigger 14 and at its opposite end to a motion transfer coupling 84 configured to convert linear movement of the transfer rod 82 into rotary movement of the valve stem 68 and linear movement of the valve plunger 72. The rearmost extension of the transfer rod 82 preferably includes an enlarged portion 85, which may be an integral portion of the transfer rod 82 or may be a separate element affixed to the end of the transfer rod 82 adjacent the cross-arm 86, and the forward, trigger engaging portion of the transfer rod 82 may also be enlarged, to keep the rod 82 from sliding out of the syringe body 16 when the body 12 is opened. The motion transfer coupling 84 includes a cross-arm 86 selectively connectable to the end of transfer rod 82 adjacent the vanes 62, 64 and a lost motion connection 87. The enlarged portion 85 engages against the cross-arm 86. By enlarging the contact area between the cross-arm 86 and the transfer rod 82, the engagement load of the transfer rod 82 on the cross-arm 86 will not cause pitting, and the engagement point between the two elements can be spread over a larger area to prevent cocking of the cross-arm 86 as it is actuated rearwardly. The lost motion connection 87 is used to selectively engage a nut 88 received on a threaded rod 90 extending from the flow control valve stem 68 with the cross bar 86. One portion of the cross arm 86 engages the foremost extension of the plunger 72 from the three way valve 64, and a second portion of the cross-arm 86 partially forms the lost motion connection 87 to selectively, linearly move the lead nut 88 received over the threaded rod 90. The lead nut 88 is fixed against rotation and the threaded rod 90 is fixed against linear movement. Therefore, linear movement of the lead nut 88 with respect to the threaded rod 90 causes the threaded rod 90 to rotate and thereby rotate the stem 68 to open the flow control valve 62. By varying the linear movement of the lead nut 88 with respect to the valve 62, the extent of stem 68 rotation may be controlled to throttle the opening through the flow control valve 62 and thus control the pressure at the piston 52.

The lost motion connection 87 includes a secondary rod 89 extending rearwardly from the cross-arm 86 and through a counter-bored hole 91 in the lead nut 88. The end of the secondary rod extending from the cross-am terminates in a shoulder, such as a secondary nut 93 received on the secondary rod 89 rearwardly of the lead nut 88. The counter-bored hole 91 terminates within the lead nut 88 in a ledge 95, and a ledge spring 97 extends about the secondary rod 69 between the secondary nut 93 and the ledge 95.

Figure 3:
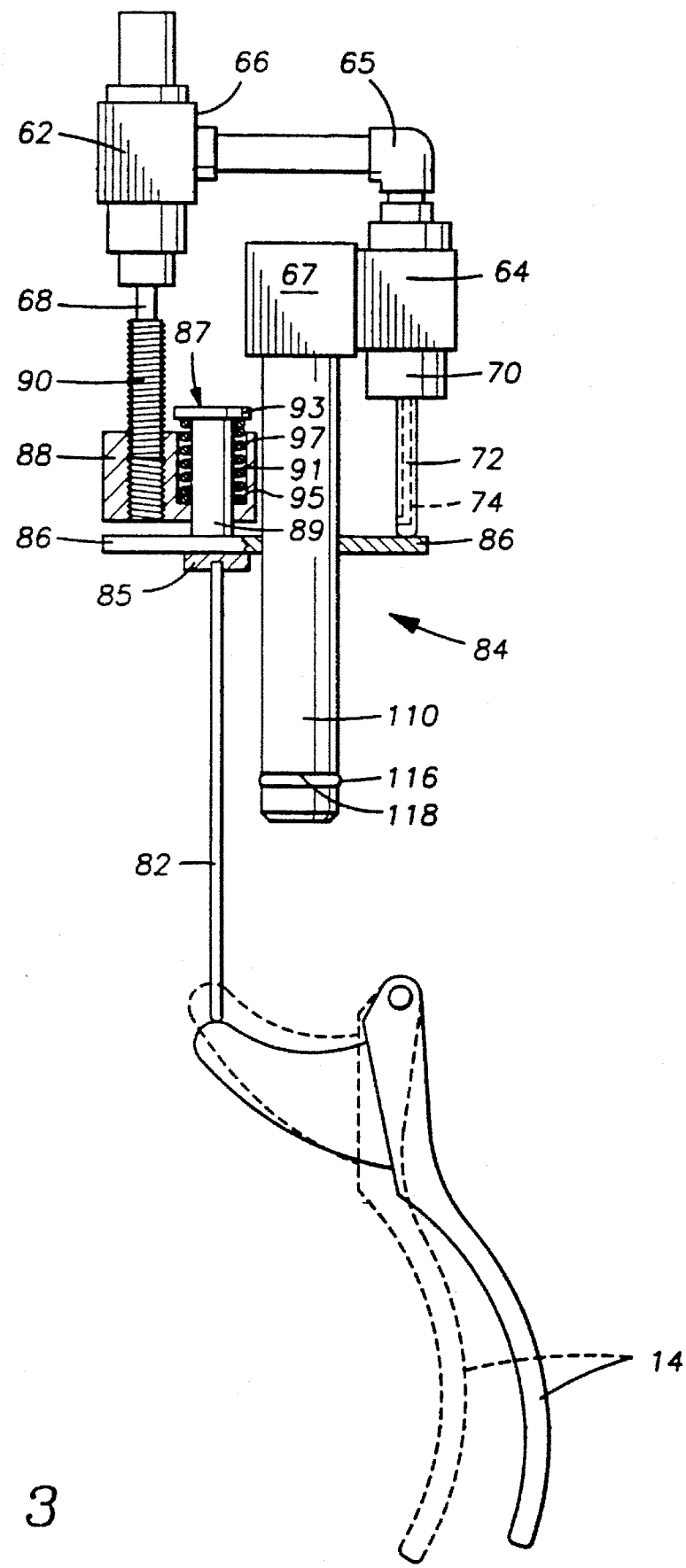
FIG. 3 is a partial sectional view of the control valve system of the delivery device of FIG. 1 in the closed, or non-delivery position.
Figure 4:
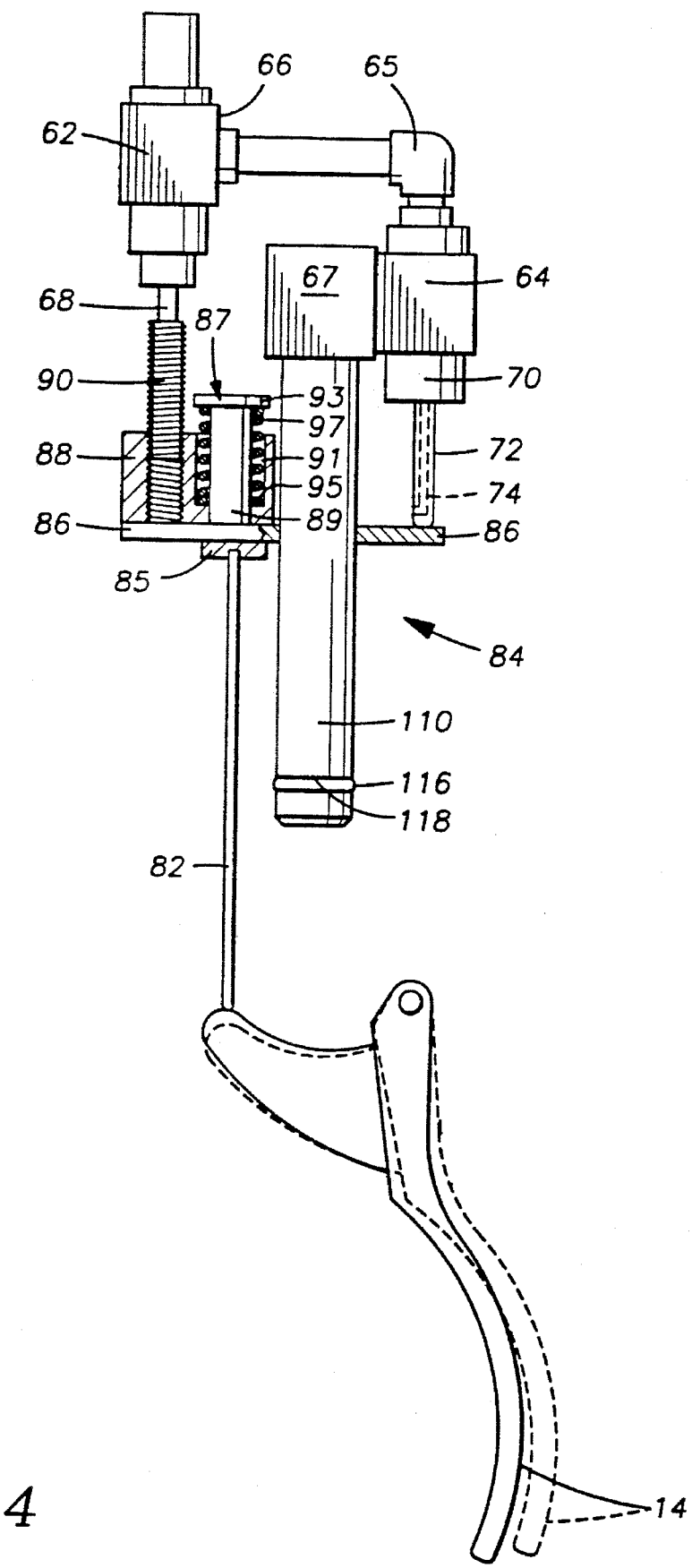
FIG. 4 is a partial sectional view of the control valve system of the delivery device of FIG. 1 wherein the trigger has been partially depressed to close the control system relief bore.

The control assembly is normally maintained in a closed position, as shown in FIG. 3, wherein the relief passage 74 in the three-way valve 64 is open to relieve pressure on the downstream side of the three way valve 64, and the main flow passages through the valves 62, 64 are closed. In this position, the cross-arm 86 is in contact with the plunger 72 of three way valve 64, but is spaced from the lead nut 88. The spring 97 biases the lead nut 88 to its fully forward position at which the valve 62 is closed. Lost motion connection 87 is used to connect the lead nut 88 to the cross arm 86. The spring 93 in the lost motion connection 87 moves the lead nut 88 to its forward most position, i.e., where the flow control valve 62 is closed, as the cross arm 86 moves forward, but it allows the cross arm 86 to move further forwardly with respect to the forward most position of the lead nut 88 to ensure that the three way valve 64 is closed and the relief passage of the three way valve 64 is opened. As the trigger 14 is depressed to the position shown in FIG. 4, the plunger 72 in the three-way valve 64 is moved inwardly of the three-way valve 64 to close the relief passage 74. At about this point the cross arm 86 also contacts the lead nut 88, although slight additional rearward movement of the cross arm 86 may be needed to engage the cross arm 86 against the lead nut 88. As the trigger 14 is pressed further inwardly of the body 12 to the position shown in FIG. 5, the cross arm 86 moves the plunger 72 of the three way valve 64 further inwardly of the three-way valve 64 and simultaneously moves the lead nut 88 linearly with respect to the threaded rod 90.

Figure 5:
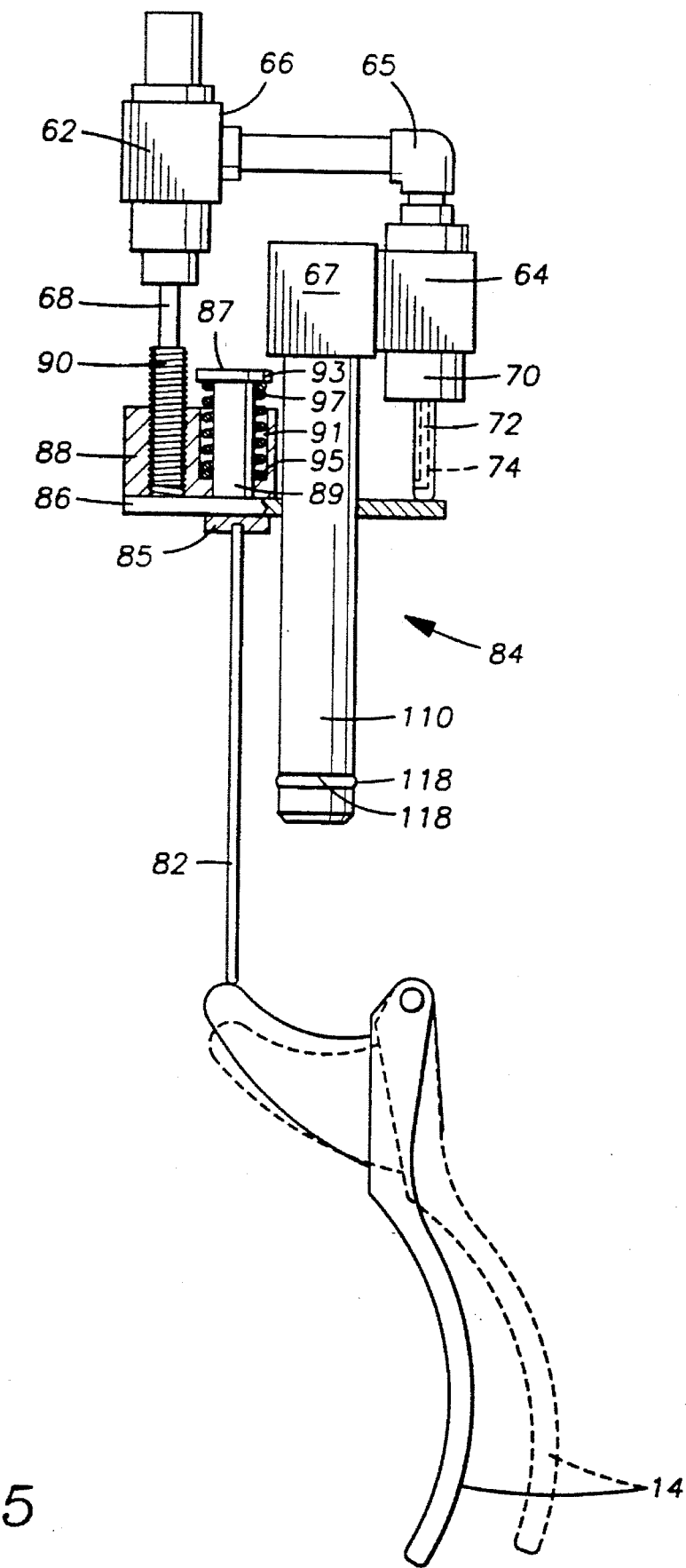
FIG. 5 is a partial sectional view of the control valve system of the delivery device of FIG. 1 in the fully open position.

The movement of the plunger 72 inwardly of the three-way valve 64 to the position shown in FIG. 5 opens the flow passage through the three-way valve 64, and the linear movement of the lead nut 88 on the threaded rod 90 causes the threaded rod 90, and the stem 68 attached thereto, to rotate to open the flow control valve 62. This allows the pressurized gas to travel through the control system 60 and tube 110 (FIG. 2) and then into the syringe body 46 behind the piston 52. This pressurized gas moves the piston 52 against the volume of collagen dispersion or solution 54 in the syringe body 46 to displace collagen dispersion or solution through the needle 48 and into the injection site.

Once the desired quantity of collagen has been delivered to the injection site, the practitioner can stop delivery of the collagen dispersion or solution by releasing the trigger 14. Once the trigger 14 is released, the spring-loaded plunger 72 actuates outwardly from the three-way valve 64 and also pushes the cross arm 86 and the transfer rod 88 attached thereto away from the body 70 of the three way valve 64. As the cross arm 86 moves forward in the valve housing 18, the secondary nut 93 on the secondary rod 89 also moves forward, and this compresses the spring 97. The spring 97 pushes on the ledge 95 on the lead nut 88, to move the lead nut 88 forward and rotate the threaded rod 90 to close the valve 62. Because the spring 97 transfers the force from the plunger 74 to move the lead nut 88 forward, the spring 97 may be configured to supply sufficient force to close, but not over-tighten, the stem 68 of the valve 62. Alternatively, the spring 97 can be removed such that secondary nut 93, or other structure forming a stop shoulder, is used to pull the lead nut 88 forward to close the flow control valve 62.

The delivery device 10 is particularly suited to supplying a continuous stream of controlled amounts of collagen dispersion or solution to the injection site while the tip of needle 48 tip is maintained in the injection site, which allows the delivery device practitioner to provide a precise amount or quantity of collagen needed to provide the desired cosmetic effect at an injection site, for example. By varying the inward travel of the trigger 14, the practitioner can change the opening of the passage through the needle valve 62 and thus throttle the pressure passing through the control system 60 to control the movement of the piston 52 in the syringe 40. Thus, the practitioner may inject collagen in one continuous stream by maintaining the trigger 14 in a fully or partially depressed position for the entire injection, can fluctuate the trigger between fully on and fully off positions to provide intermittent small quantities of collagen to the injection site, or may vary the trigger depression to continuously vary the flow rate and quantity of the collagen being delivered though the needle 48 and into the injection site. Thus, the delivery device 10 allows the practitioner a wide range of application and delivery regimens in a single package.

Referring now to FIGS. 1 and 2, the preferred supply configuration for the pressurized gas source is also shown. A pneumatic supply 100, such as a $CO_2$ bottle 102 (shown in phantom), is connected to a regulator 104. The $CO_2$ bottle 102 is received in a housing 108, and the housing 108 is sized to permit the practitioner to slip the entire pneumatic supply 100 into a pocket or clip the pneumatic supply 100 to an article of clothing. The regulator 104 is preferably a standard spring biased piston configuration (not shown) wherein a spring loads a piston against an orifice in communication with the $CO_2$ source. The piston moves on and off the orifice to regulate the pressure of the $CO_2$ on the downstream side of the valve. An adjustment knob 150 is provided on the exterior of the regulator 104, which when turned can increase or decrease the spring compression. A higher spring compression will result in a lower pressure reaching the control valve system 60. A relief vane 114 is also provided on the pneumatic supply 100. The relief valve is one typical of those in the art, which spring loads a valve on a seat. If the pressure at the relief valve 114, which is located intermediate the regulated outlet from the $CO_2$ bottle and the delivery device 10, exceeds a pre-determined limit, the relief valve 114 will vent the pressurized fluid to atmosphere. Further, if the practitioner wants to determine whether the $CO_2$ bottle 102 is still charged, or wishes to fully vent the bottle 102, the relief valve 114 may be depressed to vent the fluid to the atmosphere. The regulator 104 thus reduces the pressure of the gas exiting the bottle, typically maintained at pressures as high as 850 psi, to useable pressures of 60 to 250 psi. A length of tubing 122 extends from the regulator 104 to the fitting on the fitting portion 22 of the delivery 22 device body 12 to deliver regulated fluid to the control valve system 60. The tube 122 preferably terminates in a luer fitting with a valve, such as a poppet valve, therein. Referring again to FIG. 2, to provide a gas path from the three-way valve 64 outlet to the piston 52, the transfer tube 110, a hollow rod, extends from an elbow 67 hard piped to the three way valve 64 and into the rear open end of the syringe body 46. The transfer tube 110 includes an enlarged stop 112, which engages the back side of the syringe flange 42, and a seal ring 116 such as an o-ring seal in a seal groove 118 on the portion thereof received in the syringe body 46. Thus, as the fluid, preferably $CO_2$ in the gas phase, passes from the regulator 104, it is passed through the tubing 122, valves 62, 64 and the transfer tube 110 to contact the piston 52. A spacer 120 may be located between the terminus of the transfer tube 122, in the syringe body 46, and the piston 52 to reduce the quantity of gas charged into the syringe during each actuation of the trigger 14 where the quantity of collagen dispersion or solution in the syringe 40 is less than the full capacity of the syringe 40. If desired, the spacer 120 may be fixed to the piston 52, such as by providing a threaded stud on the spacer 120 and threading the stud into a threaded hole in the piston 52.

The delivery device 10 of the present invention is easily assembled and disassembled to allow the practitioner to remove and replace pre-filled collagen syringes 40. Referring again to FIG. 2, the delivery device is assembled by placing a fresh pre-filled syringe 40 of collagen in the syringe housing 16. The valve housing 18, with the control system 60 therein and the transfer tube 110 projecting therefrom, are then aligned with the syringe housing 16, and the two housings 16, 18 are brought together such that the free end of transfer tube 110 and the seal ring 116 portion of transfer tube 110 is received in the open end of the syringe 40 in the syringe housing 16. The housings 16, 18 are then brought together to align the fitting portions 20a, 20b thereof, and the housings 16, 18 are twisted together to lock them together about the fitting 20. To remove the syringe 40 and replace it with a new syringe 40, the sequence is reversed to open the housings 16, 18 and expose the syringe 40 for removal.

Figure 6A:
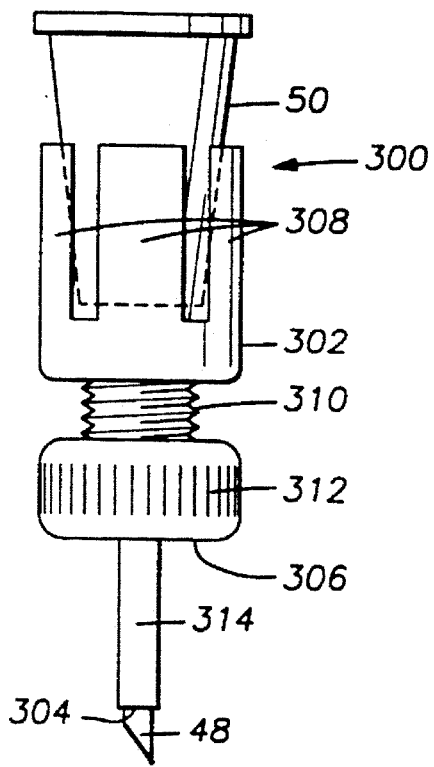
FIG. 6A is an enlarged view of the needle depth guide of the delivery device of the present invention.
Figure 6B:
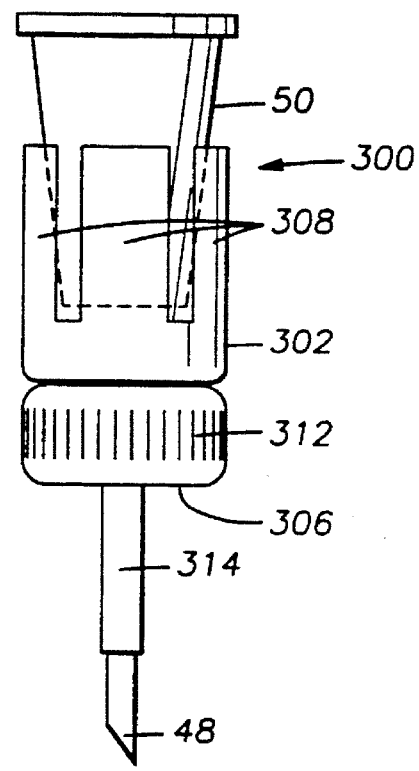
FIG. 6B is an enlarged view of the needle depth gauge of FIG. 6A moved to a second position.

Referring now to FIGS. 6A and 6B, the configuration of the needle depth guide 300 is shown. The needle depth guide 300 is used to allow a practitioner to select a specific extension of the needle tip beyond the end of the depth guide which corresponds to the desired depth of the injection, and then insert the needle until the skin, or other membrane into which the injection is being made, contacts the depth guide. In FIG. 6A, the needle 48 extends the minimum distance from the depth guide 300, and in FIG. 6B, the needle extends the maximum distance from the depth guide 300. The preferred depth guide 300 configuration includes a cap 302 which is received over the extending luer fitting 50 of the syringe 40, and an adjustable ferrule 306. The cap 302 includes a plurality of extending tines 308 which are spaced about the perimeter of the lower portion of the cap 302 and an extending threaded portion 310. The ferrule 306 includes an internally threaded first portion 312 and an extending tubular guide 314 which terminates in an open end 304. The extending tines 308 position and secure the cap 302 on the ribbed luer fitting 50 of the syringe 40. Preferably the luer fitting 50, with the needle depth guide 300 thereon, is supplied to the practitioner separately from the syringe 40, and the practitioner connects the luer fitting 50 over the distal end portion 41 of the syringe 40.

By turning the ferrule 306 on the threaded portion 310 of the cap 302, the position of the end 304 of the tubular guide 314 may be changed with respect to the distal end of the needle 48, and thus the extension of the needle 48 beyond the end 304 of the tubular portion 314 may be adjusted. The extension of the needle 48 past the end 304 of the tubular portion 314 may be used to set the depth below the skin to which the needle 48 penetrates. Thus, for a cosmetic application, when a specific quantity of collagen, or other material, is delivered to the dermis with the delivery device, the practitioner adjusts the depth guide 300 so that the desired needle 48 penetration depth under the epidermis is equal to the extension of the needle 48 beyond the end of the tubular guide 314. Preferably, the depth guide 300 is configured to allow the distal end portion of the needle 48 to extend between about 0.030 and 0.160 inches from the end of the tubular guide 314 to ensure that the collagen, or other material, is delivered to the appropriate layer of the dermis.

By turning the ferrule 306 on the threaded portion 310 of the cap 302, these dimensions for the extension of the needle end past the open end 304 of the tubular guide 314 may be provided. When the ferrule 306 is fully inwardly turned over the threaded portion 310 of the cap 302, the threaded first portion 312 engages the outer end of the cap 302 which provides the stop to ensure that no more than 0.160 inches of needle 48 will extend past the open end 304 of the tubular guide 314. Likewise, the threads on the threaded portion 310 terminate such that the ferrule 306 cannot be turned in a direction counter from the fully retracted position to a position wherein less than 0.030 inches of needle 48 extend past the end 304 of the tubular portion 314.

It is specifically contemplated that the practitioner will set the needle depth by turning the ferrule to obtain the desired needle 48 extension, and then permit the end 304 of the tubular portion 314 to touch the patient's epidermis. However, the end 304, when calibrated by the practitioner to represent a reference point for the amount of needle 48 extending therepast, may move the needle tip within the patient with fine control by using the end 304 as a reference point.

Although the delivery device 10 has been principally described with reference to the delivery of collagen to dermal locations, the delivery device 10 may also be used to control the delivery of collagen, and other injectable materials, to other locations and through delivery vehicles other than needles. For example, the device could be used to provide control over catheter delivered collagen to locations such as the urinary sphincter, or other more internal locations within the body. The delivery device 10 is particularly suited to that, and other applications, where a relatively precise quantity of material must be delivered to a specific body location. Additionally, in any application, the device 10 supplies all of the energy needed to force the injectable material from the syringe body and into the injection site, and thus reduces the muscle strain on the practitioner's hand which may accompany traditional injection techniques. Further, although the device has been described in terms wherein the control valve assembly 60 and the trigger 14 are incorporated into the device body 12, the invention specifically contemplates placing either, or both, of these elements in a separate structure, such as a foot petal housing. In that configuration, the practitioner's hands are completely freed of any triggering motions.

The above-described preferred embodiments of the present invention are not intended to limit the scope of the present invention as demonstrated by the claims which follow, as one skilled in the art can, with minimal experimentation, extend the disclosed concepts of the invention to the scope of the invention as claimed herein.

We claim:

1. A delivery device for delivering a measurable quantity of an injectable material from a syringe to an injection site, wherein the syringe includes at least a body portion for receiving a quantity of the injectable material, a delivery vehicle coupled to the body portion and insertable at an injection site and configured to permit the injectable material to pass therethrough, and a piston disposed in said body portion and moveable therein to displace at least a portion of the injectable material through the delivery vehicle, comprising:

a fluid source coupled to the syringe to provide fluid under pressure to the piston;

a control valve assembly disposed intermediate said fluid source and said piston and including a first valve member and a second valve member;

said first valve member having a valve body with a first flow passage therethrough and a plunger, having a relief bore therein, selectively positionable in said valve body, said first flow passage having an inlet and an outlet, said plunger having at least a first position wherein fluid is blocked from passage through said first flow passage and said relief bore is maintained in fluid communication with said outlet, an intermediate position wherein said relief passage is blocked from communication with said outlet and fluid is blocked from passage through said flow passage, and a second position wherein fluid may flow through said first valve member;

said second valve member having a second flow passage therethrough and a throttling member selectively engageable with said second flow passage, said throttling member having a first position wherein said throttling member closes said second flow passage to block the passage of fluid therethrough and a second position to open said second fluid passage to allow fluid to flow therethrough;

and a control member selectively positionable to position said first valve member and said second valve member in said first and said second positions.

2. The delivery device of claim 1, further including a body portion wherein the syringe body is at least partially received in said body portion.

3. The delivery device of claim 2, wherein said control member includes a trigger member arcuately positionable with respect to said body portion, said trigger member moveable between a fully extended position and a fully depressed position.

4. The delivery device of claim 1, wherein said control member further includes a cross-arm connected to said transfer rod adjacent said first valve and said second valve, and said cross arm is actuable between a first position and an intermediate position to move said plunger of said first valve between said first position and said intermediate position independently of movement of said throttling member of said second valve.

5. The delivery device of claim 4, wherein said cross arm is further actuable between said intermediate position and a second position to simultaneously actuate said plunger to open said first valve and said throttling member to open said second valve.

6. An apparatus for selecting the penetration depth of the end of a tubular delivery vehicle into a membrane, comprising:

a body portion having the tubular delivery vehicle extending therefrom, said body portion having a receptacle therein in communication with said tubular delivery vehicle;

an first member received on said body portion and fixed with respect to the tubular delivery vehicle; and a second member received on said adjustment member and selectively positionable thereon, said second member having a distal end portion disposed adjacent to the end of said delivery vehicle and adjustable with respect thereto by selectively positioning said second member on said first member.

7. The apparatus of claim 6, wherein said first member includes threads thereon, and said second member includes mating threads thereon.

8. The apparatus of claim 6, wherein said tubular delivery vehicle is a hypodermic needle.

9. The apparatus of claim 8, wherein said body member includes a luer fitting, and said first member is selectively receivable on said luer fitting.

10. The apparatus of claim 6, wherein said distal end portion extends around the delivery vehicle.

11. The apparatus of claim 10, wherein: said first member includes a threaded portion; and said second member includes an internally threaded portion received over said threaded portion and an extending tubular portion extending circumferentially about said tubular delivery vehicle.

12. The apparatus of claim 11, wherein said second member may be positioned at a first position with respect to said threaded portion at which said tubular delivery vehicle extends a maximum distance from said second member, at a second position with respect to said threaded portion at which said tubular delivery vehicle extends a minimum distance from said second member, and at intermediate positions between said first position and said second position.

13. The apparatus of claim 6, wherein said membrane is a human dermis.

14. A method of injecting an injectable material into a membrane, comprising the steps of:

provoding a delivery vehicle insertable into the membrane;

providing an adjustable guide member adjacent the end of the delivery vehicle;

selecting a distance within the membrane at which to terminate the extension of the delivery vehicle into the membrane; and positioning the guide member a distance from the tip of the delivery vehicle corresponding to the distance within the membrane at which the extension of the delivery vehicle is to terminate.

15. The method of claim 14, wherein said delivery vehicle is a hypodermic needle extending from the end of a syringe body.

16. The method of claim 15, wherein said syringe body includes threads on the end thereof, and the guide member includes threads therein and is engageable over the threads on the syringe body.

17. The method of claim 16, wherein the step of positioning the guide member is provided by rotating the guide member on said threads on said syringe body.

18. A method of injecting a material maintained in a syringe body having a tubular delivery vehicle extending therefrom and insertable into a membrane, comprising the steps of:

providing a hand-holdable body having an aperture therethrough for receiving the syringe body in a position whereby the tubular delivery extends from the hand-holdable body;

providing a pressurized fluid source;

providing a fluid control member selectively engageable between a fully open position wherein fluid is supplied to the syringe under pressure, a fully closed position wherein fluid is prevented from passing through the control member and any fluid pressure in the syringe body is vented to atmosphere, and intermediate positions between the fully open and fully closed positions wherein the pressurized fluid flow through the control member is throttled between the flow rate at the fully open and the fully closed positions.

* * * * *